US008740842B2

(12) United States Patent
Weber et al.

(10) Patent No.: US 8,740,842 B2
(45) Date of Patent: Jun. 3, 2014

(54) KERSTPIEK TIP FOR MEDICAL DEVICES

(71) Applicant: Boston Scientific Scimed, Inc., Maple Grove, MN (US)

(72) Inventors: Jan Weber, Maastricht (NL); James M. Anderson, Fridley, MN (US); Robert Chang, Belmont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/754,175

(22) Filed: Jan. 30, 2013

(65) Prior Publication Data

US 2013/0204184 A1    Aug. 8, 2013

Related U.S. Application Data

(60) Provisional application No. 61/595,825, filed on Feb. 7, 2012.

(51) Int. Cl.
*A61M 29/00* (2006.01)
(52) U.S. Cl.
USPC ........................................ 604/96.01
(58) Field of Classification Search
USPC .............. 604/96.01, 101.01, 103.07
See application file for complete search history.

(56) References Cited

U.S. PATENT DOCUMENTS

| 3,970,090 | A | * | 7/1976 | Loiacono | 604/104 |
| 5,019,042 | A | * | 5/1991 | Sahota | 604/101.01 |
| 5,902,254 | A | * | 5/1999 | Magram | 600/585 |
| 5,916,227 | A | | 6/1999 | Keith et al. | |
| 6,423,052 | B1 | * | 7/2002 | Escano | 604/523 |
| 6,488,653 | B1 | * | 12/2002 | Lombardo | 604/103.06 |
| 8,221,349 | B2 | * | 7/2012 | Auyoung et al. | 604/96.01 |
| 2004/0024419 | A1 | | 2/2004 | Slepian et al. | |

FOREIGN PATENT DOCUMENTS

WO    9807390 A1    2/1998

* cited by examiner

*Primary Examiner* — Nicholas Lucchesi
*Assistant Examiner* — Diva K Chander
(74) *Attorney, Agent, or Firm* — Seager, Tufte & Wickhem LLC

(57) ABSTRACT

An apparatus may include a medical device including an elongate shaft disposed about a guidewire, and a distal tip including a plurality of rounded protrusions, wherein adjacent protrusions are fixed directly to each other by a discrete, relatively flexible connector. The plurality of protrusions may each decrease in size from a proximalmost protrusion distally to distalmost protrusion.

18 Claims, 9 Drawing Sheets

KERSTPIEK TIP FOR MEDICAL DEVICES

CROSS-REFERENCE TO RELATED APPLICATIONS

This application claims the benefit of U.S. Application Ser. No. 61/595,825, filed Feb. 7, 2012.

TECHNICAL FIELD

The disclosure relates generally to percutaneous medical devices and more particularly to percutaneous medical devices having a large size.

BACKGROUND

Percutaneous medical devices may vary across a broad range of sizes, from the very small (in length, cross-section, or sheer bulk) to the very large. As the size of a medical device increases, the risk or potential for navigational difficulty through the vasculature and/or abrasion or injury to the walls of the vessel(s) through which the medical device travels also increases. For example, a large medical device, such as some used in certain angioplasty, atherectomy, stent-deployment, transcatheter aortic valve implantation (TAVI), valvectomy, valvuloplasty, or other intravascular procedures, may be difficult to navigate through tortuous vasculature. Similarly, such large medical devices may also present increased risk of abrasion to the vessel walls as they navigate turns or narrowing lumens. A continuing need exists for improved percutaneous medical devices and methods.

SUMMARY

An apparatus may comprise a medical device including an elongate shaft disposed about a guidewire, and a distal tip including a plurality of rounded protrusions, wherein adjacent protrusions are fixed directly to each other by a discrete, relatively flexible connector. The plurality of protrusions may each decrease in size from a proximalmost protrusion distally to distalmost protrusion.

Although discussed with specific reference to use within the coronary vasculature of a patient, for example a tortuous aorta, medical devices and methods of use in accordance with the disclosure can be adapted and configured for use in other parts of the anatomy, such as the digestive system, the respiratory system, or other parts of the anatomy of a patient.

Figure 1:
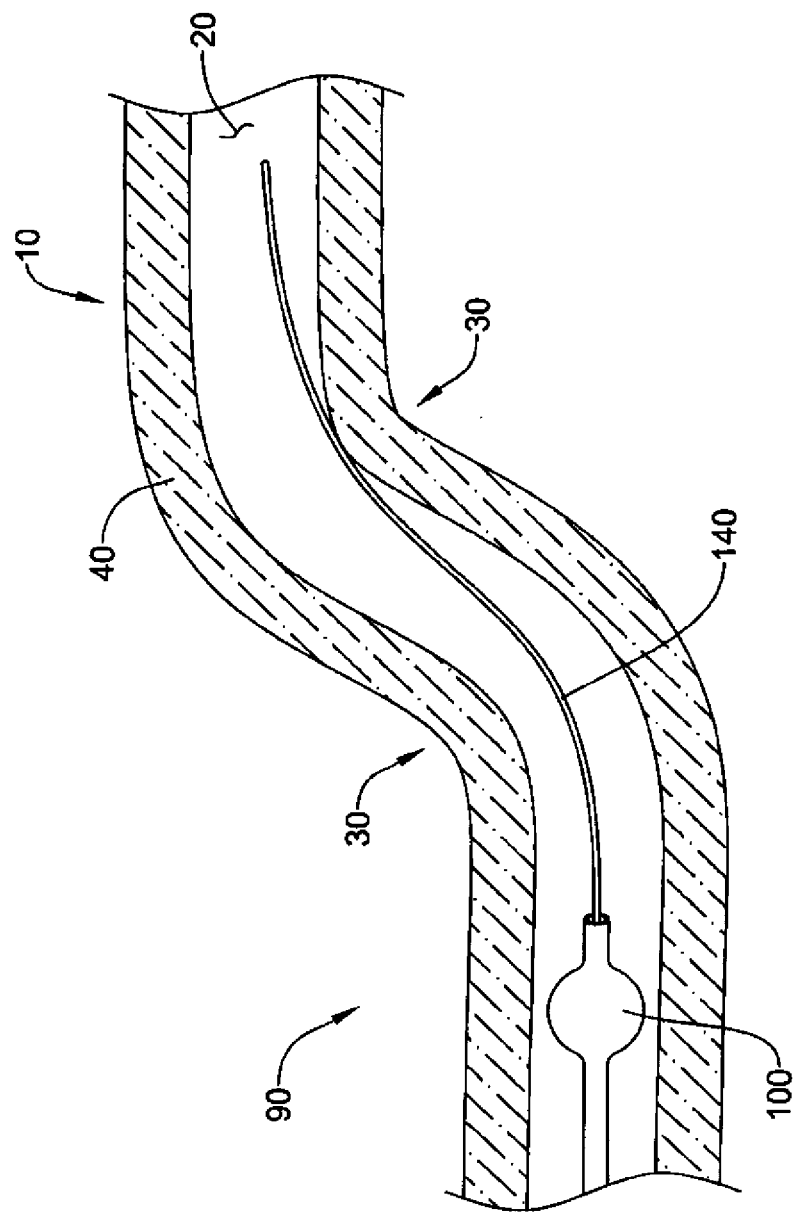
FIG. 1 is a schematic partial cross-sectional view of an example of a tortuous vessel.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

The terms "upstream" and "downstream" refer to a position or location relative to the direction of blood flow through a particular element or location, such as a vessel (i.e., the aorta) or vessel lumen, a heart valve (i.e., the aortic valve), and the like.

The term "kerstpiek" generally refers to a traditional holiday (i.e., Christmas) tree ornament placed at the top or peak of the tree. A kerstpiek may sometimes be distinguished by one or more rounded protrusions along a tapered body of the ornament. As used herein, a kerstpiek tip may generally refer to a tip or element having a shape resembling that of a traditional kerstpiek.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The detailed description and drawings are intended to illustrate but not limit the claimed invention.

A number of ailments were originally treated, if they were treatable at all, through invasive surgical techniques. Over time, less-invasive, percutaneous-access surgical techniques and medical devices have been developed to treat certain conditions. Some of those medical devices may be of substantial size, in length, cross-section, or sheer bulk, and may be relatively stiff along their length, further limiting the flexibility and navigability of the medical device(s) through tortuous vasculature, such as that illustrated in FIG. 1. As seen in FIG. 1, a tortuous vessel 10 and/or a lumen 20 thereof may include one or more sharp bends 30 requiring an apparatus 90 including a medical device 100 traversing the vessel 10 and/or lumen 20 to make turns or changes in direction. A large medical device 100 passing through the lumen 20 may scrape against a vessel wall 40 as the medical device 100 navigates the bend(s), causing injury to the vessel wall 40. Additionally, a large medical device 100 navigating through a sharp bend 30 along a guidewire 140 may cause a sharp angle to form between the guidewire 140 and the medical device 100 that may cause a kink to form in the guidewire 140 as the medical device 100 naturally wants to follow a straight path while the guidewire 140 follows the bend(s) 30 of the vessel lumen 20. A kink in the guidewire 140 may create a sharp edge or corner that could nick the vessel wall 40, thereby causing injury. Additionally, delivery of the medical device 100 over the guidewire 140 may transfer enough force to the guidewire 140, through side loading for example, to cause the guidewire 140 to cut or slice through the vessel wall 40 and/or other surrounding tissue(s) around the bend(s) 30. Further, while not explicitly illustrated, the discussion above may apply equally to the chamber(s) and/or other passages of the heart in embodiments where a medical device 100 is being advanced into and/or through the heart.

Figure 2:
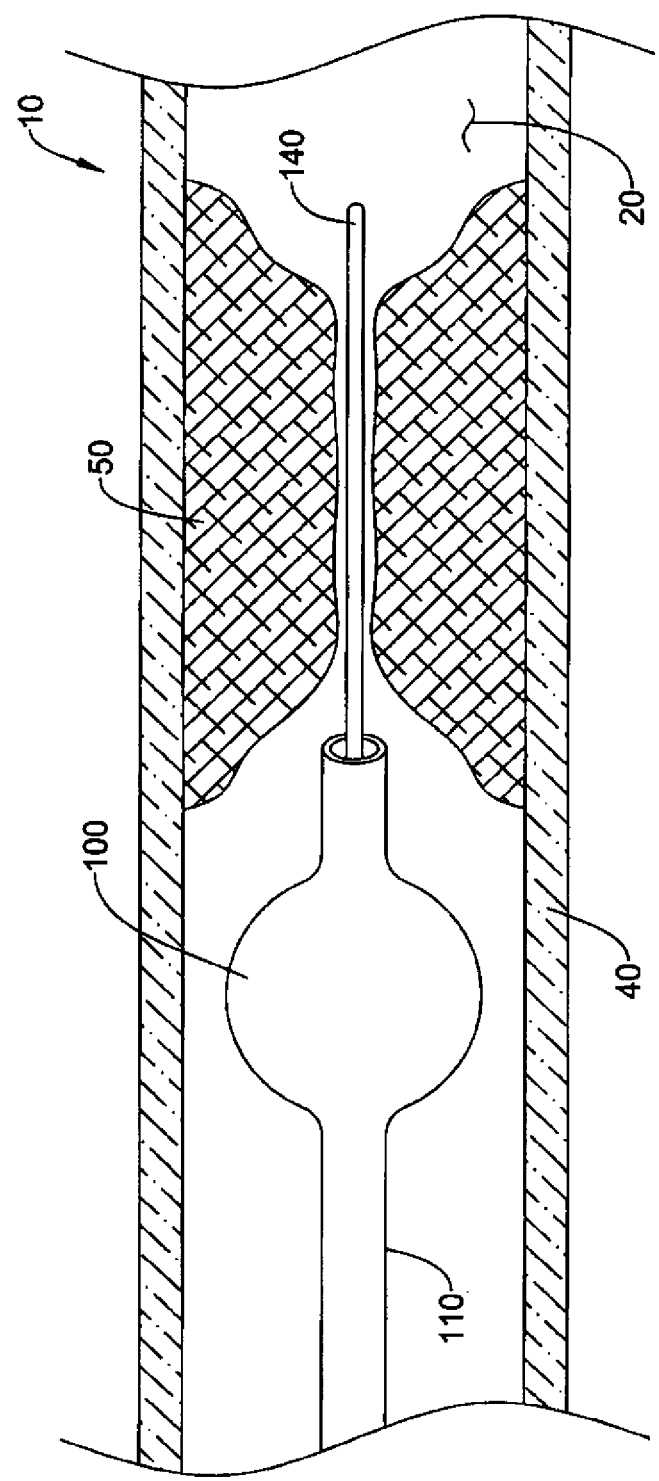
FIG. 2 is a schematic partial cross-sectional view of an example of a stenosed vessel lumen.

In some treatment procedures, an apparatus 90 including a medical device 100 may need to traverse or treat a stenosed or diseased vessel lumen 20, such as that illustrated in FIG. 2. With or without the aid of a guidewire 140, a large medical device 100 may scrape or directly impact a lesion or stenosis 50 disposed within the vessel lumen 20 adjacent or attached to the vessel wall 40, which may therefore cause vulnerable plaque, embolic material or debris, and the like to be released into the bloodstream.

Figure 3:
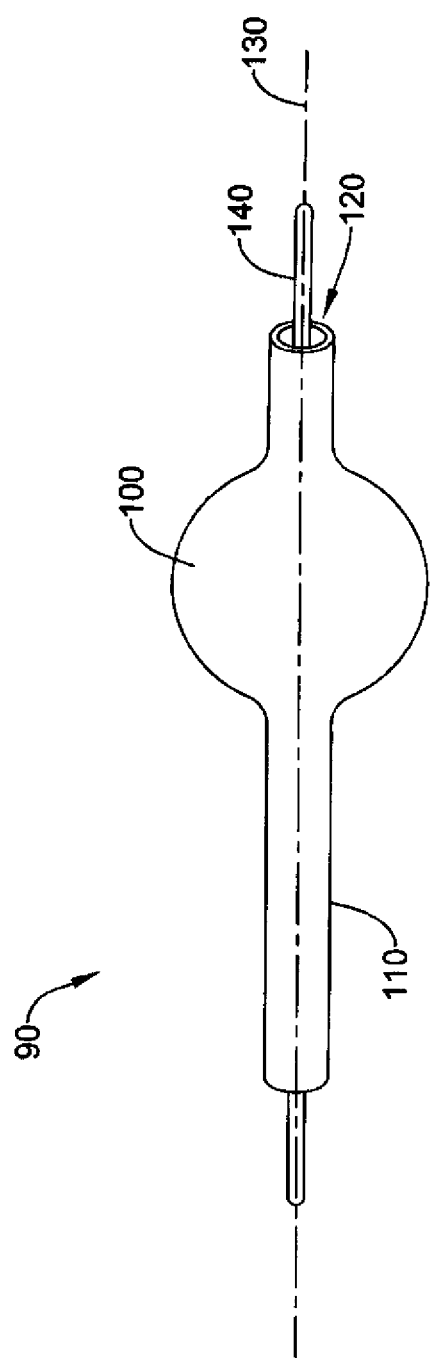
FIG. 3 is a schematic perspective view of an example apparatus including a medical device.

FIG. 3 schematically illustrates an apparatus 90 including a percutaneously-deployable medical device 100. The medical device 100 may include a portion having a large profile. Some examples of a percutaneously-deployable medical device 100 may include, but are not limited to, an angioplasty device, an atherectomy device, a balloon catheter, a stent-deployment or delivery device, a transcatheter aortic valve implantation (TAVI) device, a valvectomy device, a valvuloplasty device, or other suitable intravascular devices. A medical device 100 may include an elongate shaft 110 having a lumen 120 extending therethrough and a central longitudinal axis 130. In some embodiments, a guidewire 140 may be disposed within the lumen 120. In some embodiments, the lumen 120 may be coincident with, concentric with, and/or parallel to the central longitudinal axis 130. The medical device 100 may define an outer or radial extent measured radially outward from the central longitudinal axis 130. The medical device 100 may include a maximum outer or radial extent defined by a portion of the medical device 100 extending radially farthest from the central longitudinal axis 130 at an angle normal to the central longitudinal axis 130. In some embodiments, the portion of the medical device 100 extending radially farthest from the central longitudinal axis 130 may be disposed at a distal end of the medical device 100 or along the length of the medical device 100 at a location proximal of a distal end of the medical device 100.

Figure 4:
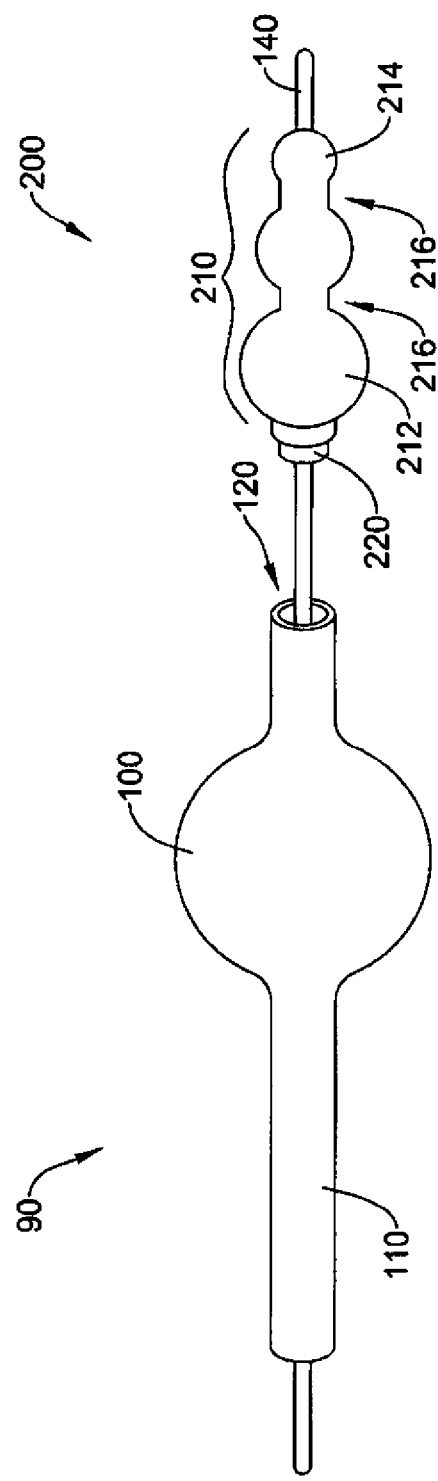
FIG. 4 is a schematic perspective view of an example apparatus including a medical device and an example kerstpiek tip.

FIG. 4 schematically illustrates an example medical device 100 including an elongate shaft 110 disposed about a guidewire 140. In some embodiments, the medical device 100 may include a distal tip 200 (i.e., a kerstpiek tip) disposed distally of the elongate shaft 110. In some embodiments, a distal tip 200 may include a lumen (not shown) extending therethrough so as to be axially slidable on, along, or about the guidewire 140 and relative to the elongate shaft 110. The distal tip 200 may include a plurality of relatively rigid, rounded protrusions 210. As the rounded protrusions 210 are a part of the distal tip 200, the plurality of rounded protrusions 210 may also have a lumen extending therethrough.

In some embodiments, the plurality of rounded protrusions 210 may be substantially spherical in shape, although other suitable rounded shapes including but not limited to elliptical, ovoid, or egg-shaped protrusions are also contemplated. In some embodiments, the plurality of rounded protrusions 210 may each decrease in size from a proximalmost protrusion 212 distally to a distalmost protrusion 214, such that the proximalmost protrusion 212 is the largest of the plurality of protrusions 210 and the distalmost protrusion 214 is the smallest of the plurality of protrusions 210. In some embodiments, a maximum outer extent of the proximalmost protrusion 212 may be sized at about 100%, 75%, 50%, 25%, or less of the maximum outer extent of the medical device 100, as measured radially from the central longitudinal axis 130.

In some embodiments, the plurality of rounded protrusions 210 may be formed of a relatively rigid and/or radiopaque material. In some embodiments, the plurality of rounded protrusions 210 may be formed of or include a metallic material, a metallic alloy, a ceramic material, a rigid or high performance polymer, a metallic-polymer composite, combinations thereof, and the like. Some examples of some suitable materials may include metallic materials and/or alloys such as stainless steel (e.g. 304v stainless steel or 316L stainless steel), nickel-titanium alloy (e.g., nitinol, such as super elastic or linear elastic nitinol), nickel-chromium alloy, nickel-chromium-iron alloy, cobalt alloy, nickel, titanium, platinum, or alternatively, a polymer material, such as a high performance polymer, or other suitable materials, and the like. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

In some embodiments, the plurality of rounded protrusions 210 may be mixed with, may be doped with, may be coated with, or may otherwise include a radiopaque material. Radiopaque materials are understood to be materials capable of producing a relatively bright image on a fluoroscopy screen or another imaging technique such as X-ray during a medical procedure. This relatively bright image aids the user of device in determining its location. Suitable radiopaque materials may include, but are not limited to, bismuth subcarbonate, iodine, gold, platinum, palladium, tantalum, tungsten or tungsten alloy, and the like.

In some embodiments, the plurality of rounded protrusions 210 may include one or more relatively flexible connectors 216 disposed between adjacent protrusions. In some embodiments, adjacent protrusions may be coupled to each other by a discrete, relatively flexible connector 216. In some embodiments, adjacent protrusions may be spaced apart by and fixed directly to each other by one discrete, relatively flexible connector 216. In other words, there may be no other elements connecting or attaching adjacent protrusions together. Similar to the rounded protrusions 210, since the flexible connector(s) 216 are a part of the distal tip 200, the flexible connector(s) 216 may also have a lumen extending therethrough. In some embodiments, the flexible connector(s) 216 may be tubular. In some embodiments, each discrete, relatively flexible connector 216 includes a maximum outer diameter that is greater than a maximum outer diameter of the guidewire and less than a minimum outer diameter of the elongate shaft 110. In some embodiments, one, some, or each of the plurality of rounded protrusions 210 may be axially translatable relative to each other. Axial translation of the flexible connector(s) 216 may permit self-alignment of the plurality of rounded protrusions 210 and adaptable flexibility.

In some embodiments, the flexible connector(s) 216 may be formed of a relatively flexible material. In some embodiments, the flexible connector(s) 216 may be formed of or include a polymeric material, a metallic or metallic alloy material, a metallic-polymer composite, combinations thereof, and the like. Examples of suitable polymers may include polyurethane, a polyether-ester such as ARNITEL® available from DSM Engineering Plastics, a polyester such as HYTREL® available from DuPont, a linear low density polyethylene such as REXELL®, a polyamide such as DURETHAN® available from Bayer or CRISTAMID® available from Elf Atochem, an elastomeric polyamide, a block polyamide/ether, a polyether block amide such as PEBA available under the trade name PEBAX®, silicones, polyethylene, Marlex high-density polyethylene, polyetheretherketone (PEEK), polyimide (PI), and polyetherimide (PEI), a liquid crystal polymer (LCP) alone or blended with other materials.

In some embodiments, the distal tip 200 may be made from, may be mixed with, may be coated with, or may otherwise include a material that provides a smooth, slick outer surface. In some embodiments, the distal tip 200, the plurality of rounded protrusions 210, and/or the flexible connector(s) 216 may include or be coated with a lubricious coating, a hydrophilic coating, a hydrophobic coating, a drug-eluting material, an anti-thrombus coating, or other suitable coating depending on the intended use or application.

In some embodiments, a distal tip 200 may include a proximal end 220 configured to mate with a distal end of the elongate shaft 110 when the distal tip 200 is translated toward and into contact with the elongate shaft 110. In some embodiments, at least a portion of the proximal end 220 may be configured to abut the distal end of the elongate shaft 110. In some embodiments, the proximal end 220 may include a stepped configuration such that at least a portion of the distal tip 200 fits within the distal end of the elongate shaft 110 and/or within the lumen 120 in a mating relationship. Although not explicitly shown, in some embodiments, the distal tip 200 may include a tapered distal end distal of the distalmost protrusion 214.

Figure 5:
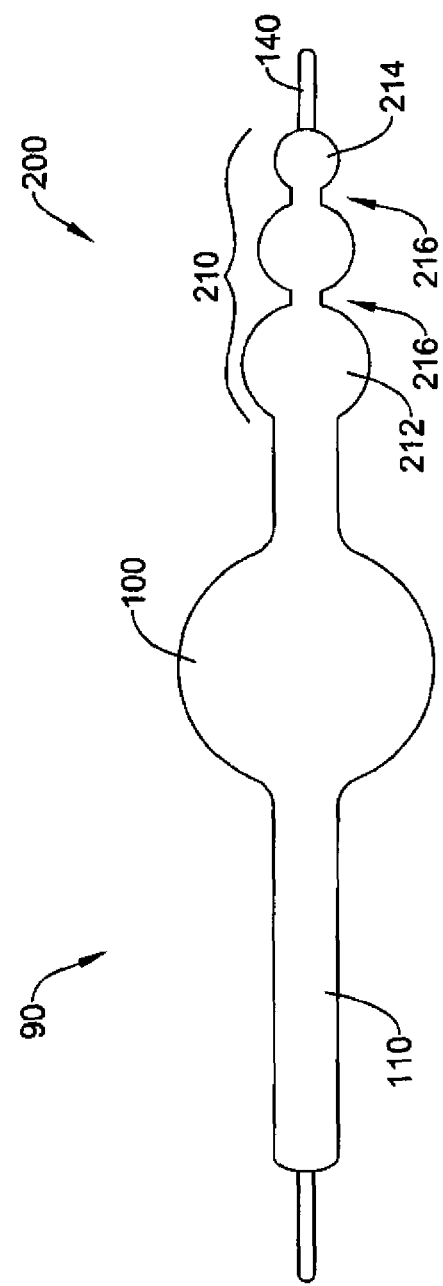
FIG. 5 is a schematic perspective view of an example apparatus including a medical device and an example kerstpiek tip.

In some embodiments, the distal tip 200 may be integrally formed with or as the distal end of the elongate shaft 110, such that the elongate shaft 110 and the distal tip 200 form a single monolithic structure, such as that shown in FIG. 5. In some embodiments, a lumen extending through the distal tip 200 may be integrally formed with the lumen 120 of the elongate shaft 110 such that a single continuous lumen extends through the entire apparatus 90, medical device 100, elongate shaft 110, and/or distal tip 200.

Figure 6B:
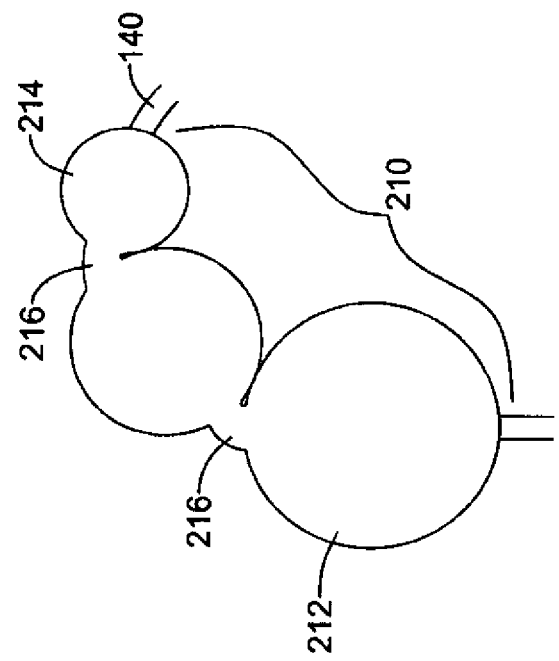
FIG. 6B is a schematic partial side view of an example kerstpiek tip in a bent condition.
Figure 6A:
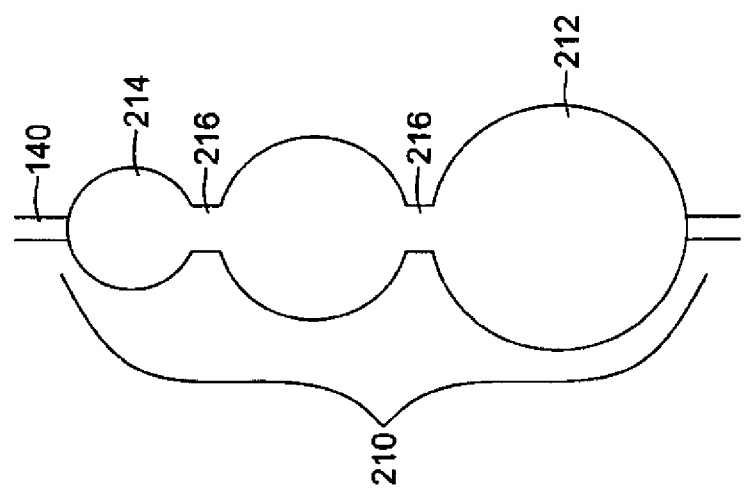
FIG. 6A is a schematic partial side view of an example kerstpiek tip in a straightened condition.

FIG. 6A illustrates an example distal tip 200 (i.e. a kerstpiek tip) in a straightened condition. As discussed above, a distal tip 200 may include a plurality of rounded protrusions 210 and one or more flexible connectors 216 disposed between adjacent protrusions. Distal tip 200 may be configured to substantially follow or slide along a guidewire 140 disposed within a lumen (not shown) extending through the distal tip 200.

In operation, an apparatus 90 including the distal tip 200 may be advanced through a vessel 10, a vessel lumen 20, bend(s) 30, and/or lesion or stenosis 50. The plurality of rounded protrusions 210 may serve to guide the medical device 100 through the vessel 10, vessel lumen 20, bend(s) 30, and/or lesion or stenosis 50. As discussed above, the relatively large profile of medical device 100 may scrape against vessel wall 40 and/or lesion or stenosis 50 as it is advanced distally. The generally tapered profile of the plurality of rounded protrusions 210 may provide a tapered distal profile to the medical device 100 thereby permitting the medical device 100 to more easily navigate the vessel 10, the vessel lumen 20, the bend(s) 30, and/or the lesion or stenosis 50 without excessive or injurious scraping of the vessel wall 40 and/or the lesion or stenosis 50.

FIG. 6B illustrates an example distal tip 200 (i.e. a kerstpiek tip) in a bent condition, such as would occur when navigating tortuous vasculature (i.e. bends 30 of vessel 10, as seen in FIG. 1) along a guidewire 140. As can be seen from FIG. 6B, the plurality of rounded protrusions 210 and the flexible connectors 216 cooperate such that at a predetermined bending angle, adjacent protrusions will come into contact with each other and thus prevent further bending of the flexible connector 216 between those adjacent protrusions that are in contact with each other. Construction of the distal tip 200 in this manner may distribute the bending along a longer section of the apparatus 90 and/or distal tip 200, so as to avoid forming a sharp angle between a guidewire 140 and a medical device 100, thereby preventing a kink from forming in the guidewire 140 which may damage or cause injury to a vessel wall 40.

Figure 7:
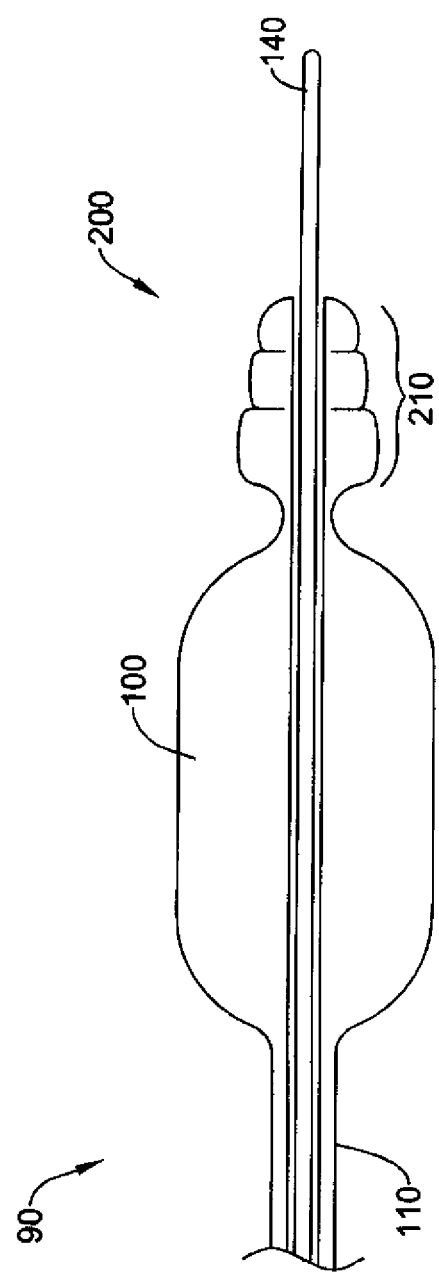
FIG. 7 is schematic partial cross-sectional view of an example apparatus including a medical device and an example kerstpiek tip.
Figure 8:
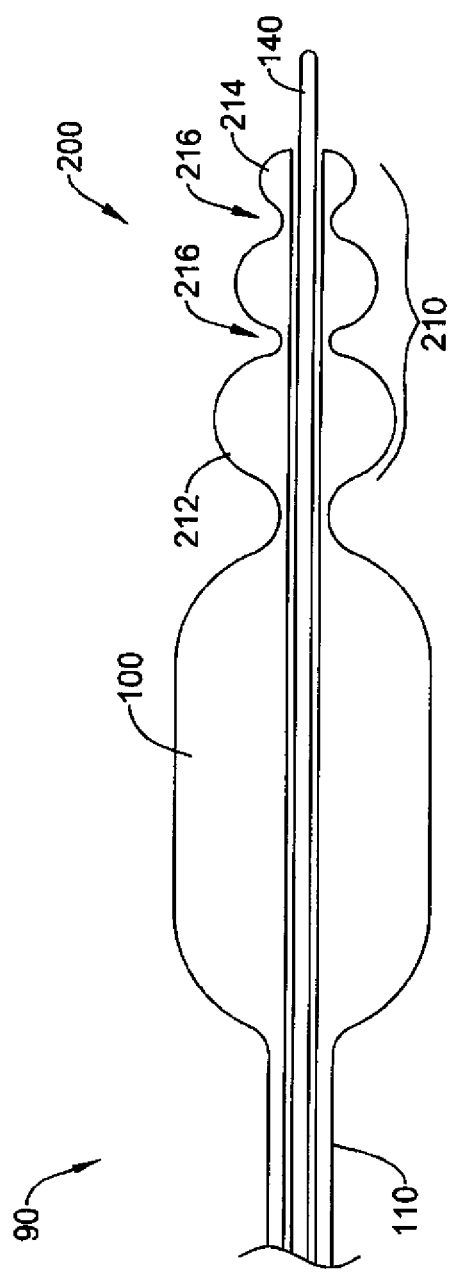
FIG. 8 is schematic partial cross-sectional view of an example apparatus including a medical device and an example kerstpiek tip.

In some embodiments, at least a portion of the distal tip 200 may be inflatable. In some embodiments, the plurality of protrusions 210 may be inflatable. In some embodiments, the distal tip 200 may form a generally conical shape tapering toward a distal end thereof when the plurality of protrusions 210 is in a deflated or collapsed condition, such as that shown for example in FIG. 7. In an inflated or expanded condition, each of the plurality of protrusions 210 may form a generally spherical shape, or other suitable shape as previously discussed, such as that shown for example in FIG. 8. In some embodiments, the distal tip 200 may be in fluid communication with an inflation lumen (not shown) extending proximally through the apparatus 90, the medical device 100, and/or the elongate shaft 110.

In some embodiments, an inflatable distal tip 200 may be used as a pre-dilatation device, a guide member, or as an atraumatic distal tip for a medical device 100. In some embodiments, an inflatable distal tip 200 may be used as an anchoring element to help prevent axial movement of the medical device 100. In some embodiments, each of the plurality of protrusions 210 of the inflatable distal tip 200 may have substantially the same internal pressures, substantially different internal pressures, or may have progressive internal pressures, when in the inflated condition. For example, the distalmost protrusion 214 may be inflated to a pressure of about 0.5 atmosphere (atm), about 1 atm, about 2 atm, about 3 atm, or other suitable pressure(s), while the proximalmost protrusion 212 may be inflated to a pressure of about 10 atm, about 12 atm, about 15 atm, about 18 atm, or other suitable pressure(s). The pressures provided herein are merely exemplary, and variation, changes, or modifications may be made without departing from the scope of the disclosure. Intervening protrusions, that is, protrusions disposed between the proximalmost protrusion 212 and the distalmost protrusion 214 may be inflated to a pressure between that of the proximalmost protrusion 212 and the to distalmost protrusion 214 and at progressively lower pressures in each protrusion toward the distalmost protrusion 214. This arrangement may also permit a variation in stiffness of the plurality of protrusions 210 according to the inflation pressures. That is, a protrusion inflated to a relatively higher pressure may be stiffer or more rigid than a protrusion inflated to a relatively lower pressure.

In some embodiments, the medical device 100 may include a balloon catheter having an inflation lumen in fluid communication with a balloon disposed at, on, or near a distal end of the elongate shaft 110. In some embodiments, an apparatus 90 may include a medical device 100 including a balloon catheter and an inflatable distal tip 200. In some embodiments, an inflatable distal tip 200 may be integrally formed with a balloon catheter. In embodiments having both a balloon catheter and an inflatable distal tip 200, the balloon catheter and the distal tip 200 may have a shared inflation lumen, or each may have a separate, discrete inflation lumen. In some embodiments having a balloon catheter and an inflatable distal tip 200, the distal tip 200 may function as a pre-dilatation device for preparing a lesion for crossing of the main balloon body.

Figure 9:
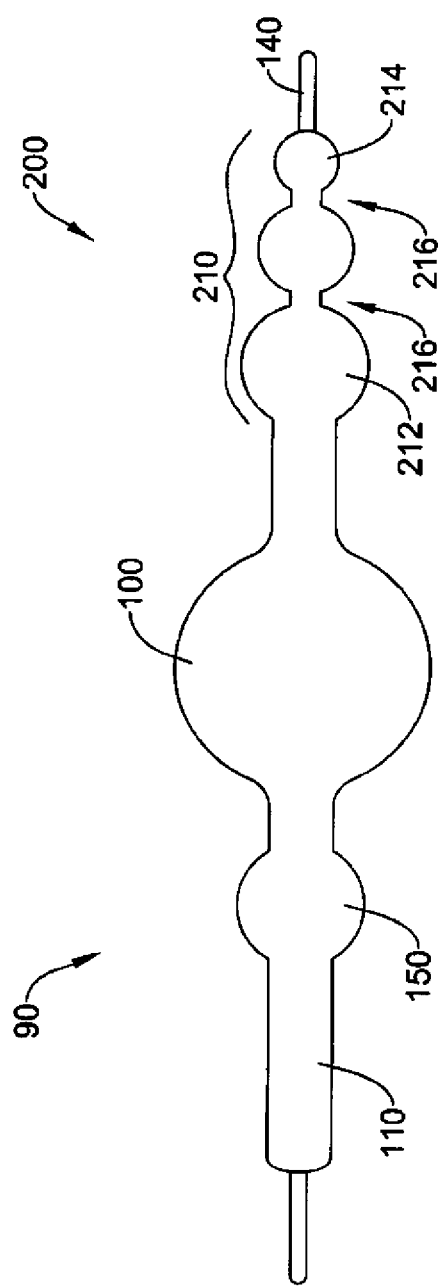
FIG. 9 is a schematic perspective view of an example apparatus including a medical device and an example kerstpiek tip.

Similar to the discussion above regarding distal advancement of the medial device 100 and the distal tip 200, withdrawal of the medical device 100 proximally through a vessel 10, vessel lumen 20, bend(s) 30, and/or lesion or stenosis 50 may also result in inadvertent or undesired scraping and/or dislodging of debris. In ways similar to those that the plurality of protrusions 210 provides advantages during distal advancement, one or more rounded protrusions 150 may be added to the elongate shaft 110 proximal of the medical device 100 to provide (at least) the same advantages during proximal withdrawal or retraction, as seen in FIG. 9. While FIG. 9 illustrates a single rounded protrusion 150, the skilled artisan art will recognize that a plurality of rounded protrusions 150 may be added or used in the same or similar manner as the plurality of rounded protrusions 210 described above. In some embodiments having a plurality of rounded protrusions 150, the plurality of protrusions 150 may each decrease in size from a distalmost protrusion proximally to a proximalmost protrusion, such that the distalmost protrusion is the largest of the plurality of protrusions 150 and the proximalmost protrusion is the smallest of the plurality of protrusions 150. In some embodiments, a maximum outer extent of the distalmost protrusion may be sized at about 100%, 75%, 50%, 25%, or less of the maximum outer extent of the medical device 100, as measured radially from the central longitudinal axis 130 (not shown).

It should be understood that although the above discussion was focused on a medical device and methods of use within the vascular system of a patient, other embodiments of medical devices or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the apparatus and/or medical devices described herein with respect to percutaneous deployment may be used in other types of surgical procedures as appropriate. For example, in some embodiments, the medical devices may be deployed in a non-percutaneous procedure, such as an open heart procedure. Devices and methods in accordance with the invention can also be adapted and configured for other uses within the anatomy.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. An apparatus, comprising:
   a medical device including an elongate shaft disposed about a guidewire; and
   a distal tip including a plurality of rounded protrusions;
   wherein adjacent protrusions are coupled to each other by a discrete, relatively flexible connector;
   wherein each discrete, relatively flexible connector includes a maximum outer diameter that is greater than a maximum outer diameter of the guidewire and less than a minimum outer diameter of the elongate shaft.

2. The apparatus of claim 1, wherein adjacent protrusions are fixed directly to each other by one discrete, relatively flexible connector.

3. The apparatus of claim 1, wherein the distal tip is disposed on the guidewire.

4. The apparatus of claim 1, wherein the plurality of protrusions each decrease in size from a proximalmost protrusion distally to distalmost protrusion.

5. The apparatus of claim 4, wherein a maximum outer extent of the proximalmost protrusion is sized at about 50% of a maximum outer extent of the medical device measured radially from a central longitudinal axis thereof.

6. The apparatus of claim 1, wherein the plurality of protrusions is relatively rigid.

7. The apparatus of claim 6, wherein the plurality of protrusions is formed from a metallic material.

8. The apparatus of claim 6, wherein the plurality of protrusions is formed from a ceramic material.

9. The apparatus of claim 1, wherein each connector is formed from a polymer material.

10. The apparatus of claim 1, wherein the plurality of protrusions is substantially radiopaque.

11. The apparatus of claim 1, wherein the distal tip is integrally formed with the elongate shaft.

12. The apparatus of claim 1, wherein the distal tip is axially slidable relative to the elongate shaft.

13. The apparatus of claim 12, wherein the distal tip is configured to mate with a distal end of the elongate shaft.

14. The apparatus of claim 1, wherein the medical device includes a balloon catheter.

15. The apparatus of claim 14, wherein the distal tip is integrally formed with the balloon catheter.

16. The apparatus of claim 1, wherein the plurality of protrusions is inflatable.

17. The apparatus of claim 16, wherein the distal tip forms a generally conical shape when the plurality of protrusions is in a deflated condition.

18. An apparatus, comprising:
    a medical device including an elongate shaft disposed about a guidewire; and
    a distal tip including a plurality of rounded protrusions;
    wherein the plurality of protrusions each decrease in size from a proximalmost protrusion distally to distalmost protrusion;
    wherein a maximum outer extent of the proximalmost protrusion is sized at about 50% of a maximum outer extent of the medical device measured radially from a central longitudinal axis thereof.

* * * * *